United States Patent
Hashizume

(10) Patent No.: US 8,461,141 B2
(45) Date of Patent: Jun. 11, 2013

(54) PREVENTIVE OR THERAPEUTIC DRUG FOR ALZHEIMER-TYPE DEMENTIA

(75) Inventor: Kiyoshi Hashizume, Nagano (JP)

(73) Assignee: Mochida Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 12/833,508

(22) Filed: Jul. 9, 2010

(65) Prior Publication Data

US 2010/0273878 A1 Oct. 28, 2010

Related U.S. Application Data

(63) Continuation of application No. 12/085,867, filed as application No. PCT/JP2006/324172 on Dec. 4, 2006, now abandoned.

(30) Foreign Application Priority Data

Dec. 2, 2005 (JP) ................................ 2005-349438

(51) Int. Cl.
*A01N 43/00* (2006.01)
*A61K 31/33* (2006.01)

(52) U.S. Cl.
USPC .......................................... 514/183; 514/549

(58) Field of Classification Search
None
See application file for complete search history.

(56) References Cited

U.S. PATENT DOCUMENTS

| | | | | |
|---|---|---|---|---|
| 5,116,873 A | * | 5/1992 | Gorio et al. | 514/567 |
| 6,936,274 B2 | * | 8/2005 | Hanshew et al. | 424/465 |
| 2002/0052404 A1 | | 5/2002 | Hunter et al. | |

FOREIGN PATENT DOCUMENTS

| | | |
|---|---|---|
| JP | 3-58926 A | 3/1991 |
| JP | 3-264524 A | 11/1991 |
| JP | 6-237734 A | 8/1994 |
| JP | 8-231391 A | 9/1996 |

OTHER PUBLICATIONS

Remington's pharmaceutical sciences, drugs, pp. 420-425.*
JP-06-237734, Machine translation.*
Flood et al, Psychopharmacology, 1985, 86:61-67.*
Nakanishi, T., "Consideration on Serum Triiodothyronine (T3), Thyroxine (T4) Concentration and T3/T4 Ratio in the Patients of Senile Dementia," Igaku Kenkyu, vol. 60, No. 1, pp. 18-25, Feb. 1990.
Otsuka, M. and A. Ueki, "Analysis of dietary factors in dementia patients and study on cognitive function-improving effect of eicosapentaenoic acid (EPA)," Dementia Japan, vol. 15, No. 1, pp. 21-29, Apr. 2001 (with English translation).
Belandia, Borja et al., "Thyroid Hormone Negatively Regulates the Transcriptional Activity of the β-Amyloid Precursor Protein Gene," The Journal of Biological Chemistry, vol. 273, No. 46, pp. 30366-30371, Nov. 13, 1998.
Boston, Paul F. et al., "Ethyl-EPA in Alzheimer's disease—a pilot study," Prostaglandins, Leukotrienes and Essential Fatty Acids, vol. 71, No. 5, pp. 341-346, XP004571556, Nov. 1, 2004.
Extended European Search Report dated Jul. 8, 2010 in Application No. 06833929.0.
Hashimoto, Michio et al., "Chronic Administration of Docosahexaenoic Acid Ameliorates the Impairment of Spatial Cognition Learning Ability in Amyloid β-Infused Rats," Journal of Nutrition, vol. 135, No. 3, pp. 549-555, XP2468170, Mar. 1, 2005.
van Osch, Liesbeth A.D.M. et al., "Low thyroid-stimulating hormone as an independent risk factor for Alzheimer disease," Neurology, vol. 62, No. 11, pp. 1967-1971, XP2588314, Jun. 8, 2004.
Office Action for Japanese Application No. 2007-548031, dated Apr. 17, 2012, including a partial English translation.

* cited by examiner

*Primary Examiner* — Brandon Fetterolf
*Assistant Examiner* — Jean Cornet
(74) *Attorney, Agent, or Firm* — Birch, Stewart, Kolasch & Birch, LLP

(57) ABSTRACT

It is intended to provide a highly safe preventive or therapeutic drug for Alzheimer-type dementia which can replace the conventional therapies currently used for Alzheimer-type dementia or which can be used together with the conventional therapy to realize high therapeutic effects, characterized in that a ω-3 polyunsaturated fatty acid and thyroid hormone are used in combination.

6 Claims, No Drawings

PREVENTIVE OR THERAPEUTIC DRUG FOR ALZHEIMER-TYPE DEMENTIA

This application is a Continuation of co-pending application Ser. No. 12/085,867 filed on May 30, 2008, which is a national phase application of International Application No. PCT/JP2006/324172 filed on Dec. 4, 2006, and this application claims priority of Application No. 2005-349438 filed in Japan on Dec. 2, 2005, under 35 U.S.C. §119; the entire contents of all are hereby incorporated by reference.

TECHNICAL FIELD

This invention relates to a novel preventive or therapeutic drug for Alzheimer-type dementia, and more specifically, to a preventive or therapeutic drug for Alzheimer-type dementia wherein an ω-3 polyunsaturated fatty acid is used in combination with a thyroid hormone.

BACKGROUND ART

With the progress of aging of the society, number of patients suffering from dementia is ever more increasing. Dementia is the condition in which acquired intelligence has persistently declined by organic disorder of brain. Dementia has been classified into several types based on the pathogenesis and histopathology, and the most typical types are Alzheimer-type dementia and cerebrovascular dementia. Conceivably, these two types of dementia and the mixed type of these two constitute 80 to 90% of the entire dementia case.

Alzheimer-type dementia is associated with atrophy of brain, and up to this moment, no drug has been found that can fundamentally treat this disease. The only commercially available pharmaceutical product with the indication for Alzheimer-type dementia is donepezil hydrochloride (trade name Aricept: manufactured by Eisai Co., Ltd.). This product, however, is indicated for "inhibition of the advance of dementia symptoms of slight or moderate Alzheimer-type dementia", and this product may not be sufficient in view of fundamental treatment of the disease.

Icosapentaenoic acid (also referred to as eicosapentaenoic acid, hereinafter abbreviated as EPA) which is a member of ω-3 polyunsaturated fatty acids is a polyunsaturated fatty acid extracted and purified from fish oil, and EPA is known for its effect of reducing serum lipids, suppressing platelet aggregation, and the like. In Japan, ethyl ester of this EPA is commercially available as a therapeutic drug for arteriosclerosis obliterans and a therapeutic drug for hyperlipidemia. EPA has been reported to retard advance of symptoms of Alzheimer-type dementia (see, for example, Non-patent document 1). This document discloses that, when the patients suffering from Alzheimer-type dementia were administered with EPA at a daily dose of 900 mg for 12 months, and the symptoms were observed (number of the evaluated case: 22), "administration of EPA to the patients of Alzheimer-type dementia resulted in the improvement of the cognitive skill for 3 to 6 months. However, after this period, the cognitive skill declined with the natural prognosis of the disease" (page 27, right column).

This document, however, does not disclose or indicate excellent effects on the Alzheimer-type dementia achieved by the combination of the ω-3 polyunsaturated fatty acid and thyroid hormone.

[Non-Patent Document]
Dementia Japan, 2001, vol. 15, pp. 21-29.

DISCLOSURE OF THE INVENTION

In view of the situation as described above, an object of the present invention is to provide a highly safe preventive or therapeutic drug for Alzheimer-type dementia which can replace the conventional therapies currently used for Alzheimer-type dementia or which can be used together with the conventional therapy to realize high therapeutic effects.

The inventors of the present invention carried out an intensive study on the preventive or therapeutic drug for Alzheimer-type dementia, and found that use of a combination of an ω-3 polyunsaturated fatty acid and a thyroid hormone exhibits excellent therapeutic effects for Alzheimer-type dementia as well as high safety. The present invention has been completed on the basis of such finding.

The preventive or therapeutic drug for Alzheimer-type dementia wherein an ω-3 polyunsaturated fatty acid is used in combination with a thyroid hormone has significant therapeutic effects for the Alzheimer-type dementia while it exhibits no adverse events, and accordingly, it should provide a highly effective preventive or therapeutic drug for Alzheimer-type dementia with high safety.

BEST MODE FOR CARRYING OUT THE INVENTION

Next, the present invention is described in detail.

According to an aspect of the present invention, the present invention provides a preventive or therapeutic drug for Alzheimer-type dementia wherein an ω-3 polyunsaturated fatty acid is used in combination with a thyroid hormone.

According to another aspect of the present invention, the present invention provides a food having a preventive or therapeutic effect for Alzheimer-type dementia wherein an ω-3 polyunsaturated fatty acid is used in combination with a thyroid hormone.

A polyunsaturated fatty acid is defined as a fatty acid having two or more carbon-carbon double bonds in the molecule, and the polyunsaturated fatty acids are further grouped by the position of the double bond into ω-3, ω-6, and other polyunsaturated fatty acids. Exemplary ω-3 polyunsaturated fatty acids include α-linolenic acid, EPA, and docosahexaenoic acid (hereinafter abbreviated as DHA). The polyunsaturated fatty acid used in the present invention may be either a synthetic or a natural polyunsaturated fatty acid, or a natural oil containing such polyunsaturated fatty acids. Synthetic products include those which have been produced by chemical synthesis, and semi-synthetic products which have been produced by microorganisms and then subjected to esterification, ester exchange, or the like. The natural products may be either those extracted from a natural oil containing polyunsaturated fatty acids by a known means or those which have been further processed to produce a crude product or further purified products. Salts of an ω-3 polyunsaturated fatty acid as well as derivatives such as ester, amide, phospholipid, monoglyceride, diglyceride, and triglyceride of a polyunsaturated fatty acid are also included within the ω-3 polyunsaturated fatty acid used in the present invention.

The ω-3 polyunsaturated fatty acid used in the present invention is preferably at least one member selected from EPA, DHA, and α-linolenic acid. Still more preferably, the ω-3 polyunsaturated fatty acid is EPA, DHA, or a mixture thereof, and even more preferably, the ω-3 polyunsaturated fatty acid is ethyl icosapentate (hereinafter abbreviated as EPA-E), ethyl docosahexaenoate (hereinafter abbreviated as DHA-E), or a mixture thereof. Most preferably, the ω-3 polyunsaturated fatty acid is EPA-E. In Japan, a soft capsule preparation containing high purity EPA-E (trade name Epadel, manufactured by MOCHIDA PHARMACEUTICAL CO., LTD.) is commercially available as a therapeutic drug for arteriosclerosis obliterans (ASO) or hyperlipidemia, and this product can be used. An example of the mixture of EPA-E and DHA-E is Omacor (a soft capsule containing about 46% by weight of EPA-E and about 38% by weight of DHA-E manufactured by Ross Products), which is commercially available in the U.S. and the like as a therapeutic agent for hypertriglyceridemia, and which may be used in the present invention. Also preferred are the embodiments wherein the ω-3 polyunsaturated fatty acid is in the form of a purified fish oil as well as the embodiments wherein the ω-3 polyunsaturated fatty acid is at least one member selected from monoglyceride, diglyceride, and triglyceride.

The purity of the ω-3 polyunsaturated fatty acid used in the composition of the present invention, namely, content of the ω-3 polyunsaturated fatty acid in the entire fatty acid is not particularly limited. However, the purity is preferably at least 25% by weight, more preferably at least 50% by weight, still more preferably at least 70% by weight, and still more preferably at least 85% by weight, and most preferably, the purity of the polyunsaturated fatty acid is such that it is substantially free from fatty acid components other than the ω-3 polyunsaturated fatty acid.

ω-3 polyunsaturated fatty acid is easily oxidized, and therefore, simultaneous incorporation of an effective amount of an antioxidant such as butylated hydroxytoluene, butylated hydroxyanisole, propyl gallate, gallic acid, a pharmaceutically acceptable quinone, or a α-tocopherol is desirable.

The thyroid hormone used in the present invention is not particularly limited as long as it exhibits the effects intended in the present invention. Exemplary thyroid hormones include levothyroxine and liothyronine, and the preferred is levothyroxine sodium (trade name, Thyradin S, manufactured by ASKA Pharmaceutical Co., Ltd.). It is to be noted that substantially same effects are realized by using a growth hormone (for example, somatropin) instead of the thyroid hormone.

The preventive or therapeutic drug for Alzheimer-type dementia of the present invention may be administered either by solely administering the effective components (possibly with other inevitable components remaining after the purification), or by forming an adequate pharmaceutical preparation with a carrier or a medium commonly used in the art such as an excipient, a binder, a lubricant, a colorant, or a flavor, optionally with sterilized water or a vegetable oil, or further with a non-toxic organic solvent or a non-toxic solubilizer (for example, glycerin or propylene glycol), an emulsifier, a suspending agent (for example, Tween 80 and or arabic solution), an isotonic agent, a pH adjusting agent, a stabilizer, a soothing agent. The food having a preventive or therapeutic effects for Alzheimer-type dementia of the present invention may also be prepared either with solely the effective component (possibly with other inevitable components remaining after the purification), or in combining with a carrier or a medium commonly used in the art as in the case of the preventive or therapeutic drug for Alzheimer-type dementia. Exemplary preferable foods include supplement, nutraceutical, food with nutrient function claims, food for specified health uses, and health food.

The pharmaceutical preparation may be administered orally, intravenously, intraarterially, by inhalation, endorectally, intravaginally, or externally in the dosage form of a tablet, a capsule, a microcapsule, granules, fine granules, a powder, an oral liquid, a suppository, a syrup, an inhalant, an ointment, an injection (emulsion, suspension, or non-aqueous), or an injection in the form of emulsion or suspension which has been prepared from a solid injection immediately before the administration. The preferred is the oral administration by encapsulating in a capsule such as a soft capsule or a microcapsule. Also preferred is intravenous or intraarterial administration in the form of an injection (emulsion, suspension, or non-aqueous) or an injection in the form of emulsion or suspension which has been prepared from a solid injection immediately before the administration.

The dose of the ω-3 polyunsaturated fatty acid of the preventive or therapeutic drug for Alzheimer-type dementia of the present invention may be an effective amount to exhibit the intended behavior which may be adequately adjusted by the dosage form, administration route, frequency of administration per day, seriousness of the symptom, body weight, age, and the like. When ethyl icosapentate is orally administered, a dose in terms of EPA-E is typically 100 to 9,000 mg/day, preferably 300 to 6,000 mg/day, and more preferably 300 to 2,700 mg/day which may be administered in 2 to 3 divided doses, or if desired in a single dose or in several divided doses.

The dose of the thyroid hormone of the preventive or therapeutic drug for Alzheimer-type dementia of the present invention may be an effective amount to exhibit the intended behavior which may be adequately adjusted by the dosage form, administration route, frequency of administration per day, seriousness of the symptom, body weight, age, and the like. When levothyroxine sodium is orally administered, a dose in terms of levothyroxine sodium of 25 to 200 μg/day may be administered once a day. Such dose, however, may be administered in several divided doses.

The combination of the daily dose of the EPA-E and the daily dose of the levothyroxine sodium is not particularly limited. However, this combination is preferably one of (1) 1,800 to 2,700 mg/day of EPA-E and 25 to 200 μg/day of levothyroxine sodium, (2) 1,800 to 2,700 mg/day of EPA-E and 25 to 100 μg/day of levothyroxine sodium, (3) 300 to 600 mg/day of EPA-E and 25 to 200 μg/day of levothyroxine sodium, and (4) 300 to 600 mg/day of EPA-E and 25 to 100 μg/day of levothyroxine sodium.

The a preventive or therapeutic drug for Alzheimer-type dementia of the present invention characterized by the combined use of an ω-3 polyunsaturated fatty acid and a thyroid hormone may be in the form of 1) combined taking of the both drugs, namely, simultaneous or separate taking of the drug containing the ω-3 polyunsaturated fatty acid and the drug containing the thyroid hormone; 2) a combined drug, namely, a drug prepared by incorporating both of the ω-3 polyunsaturated fatty acid and the thyroid hormone, and 3) a kit containing both drugs, namely, a set prepared by combining a unit dose (single dose, daily dose, etc.) of the drug containing an ω-3 polyunsaturated fatty acid and the drug containing a thyroid hormone. The preventive or therapeutic drug for Alzheimer-type dementia of the present invention include the drug containing an ω-3 polyunsaturated fatty acid and a thyroid hormone as its only effective components, namely, the drug prepared by combining an ω-3 polyunsaturated fatty acid and a thyroid hormone; and also, a preventive or therapeutic drug for Alzheimer-type dementia further comprising an effective component other the ω-3 polyunsaturated fatty acid and the thyroid hormone.

The preventive or therapeutic drug for Alzheimer-type dementia of the present invention may be used with any one of the conventional therapeutic drug for Alzheimer-type dementia as typically represented by donepezil (trade name Aricept: manufactured by Eisai Co., Ltd.). Combination with the donepezil enables improvement of the Alzheimer-type dementia whose symptoms could not be sufficiently improved by donepezil alone. Such combination also enables use of the donepezil at a reduced dose.

The preventive or therapeutic drug for Alzheimer-type dementia of the present invention wherein an ω-3 polyunsaturated fatty acid is used in combination with a thyroid hormone also includes the case in which a patient of Alzheimer-type dementia who is administered with an ω-3 polyunsaturated fatty acid (1) for the purpose of treating hyperlipidemia or ASO, (2) in the expectation of antiarteriosclerotic action, or (3) in the expectation of preventing onset of the cardiovascular event or cerebrovascular event, and in particular, a patient whose improvement of the symptom of the Alzheimer-type dementia is insufficient is further administered with a thyroid hormone. Also included in the present invention is the case in which a patient of Alzheimer-type dementia who is administered with a thyroid hormone, and in particular, a patient whose improvement of the symptom of the Alzheimer-type dementia is insufficient is further administered with a drug containing an ω-3 polyunsaturated fatty acid, and in particular, a drug containing EPA-E.

The severity of the Alzheimer-type dementia to be treated by the therapeutic drug for Alzheimer-type dementia characterized by the use of a combination of an ω-3 polyunsaturated fatty acid and a thyroid hormone of the present invention is not particularly limited. According to Reisberg, average score of Hasegawa Dementia Scale (wherein the score of up to 20 corresponds to "doubt of dementia" on a scale of 30) in each severity is such that 19.1 for slight dementia, 15.4 for moderate dementia, 10.7 for slightly advanced dementia, and 4.0 for advanced dementia.

EXAMPLES

Next, the present invention is described in further detail by referring to the Examples, which by no means limit the scope of the present invention.

Example

Subject and Method 14 patients (6 males and 8 females in their fifties to eighties) diagnosed with Alzheimer-type dementia but having no history of cerebral infarction and not suffering from primary diseases of dementia such as hypothyroidism were administered with ethyl icosapentate (trade name Epadel; manufactured by Mochida Pharmaceutical Co., Ltd.; abbreviated as "EPA-E" in the Table) at a daily dose of 300 to 600 mg for 2 months, and then, also with levothyroxine sodium (trade name thyradin S; manufactured by ASKA Pharmaceutical Co., Ltd.; abbreviated as "T4" in the Table) at a daily dose of 50 to 100 μg for 4 months in addition to the ethyl icosapentate. Each patient was evaluated for the improvement of the dementia by Hasegawa Dementia Scale at the start of the test, 2 months after the start of the test (2 months from the start of administering ethyl icosapentate), and 6 months after the start of the test (4 months after the start of the combined administration of the ethyl icosapentate and the levothyroxine sodium).

Results

The results for each case are shown in Table 1. The average score of the Hasegawa Dementia Scale is shown in Table 3 together with the average score of Reference Examples. As shown in Table 1, when the change in symptoms was observed after the test period of 6 months, improvements such as willingness, refection, increase in the habitat, and lucidity were noted. In addition, improvement in the score of Hasegawa Dementia Scale was noted in substantially all cases. Average score of the Hasegawa Dementia Scale at the start of the test was 10.0, and this average score increased to as high as 16.8 at the end of the test period (6 months after the start of the test). Improvement in the symptoms was noted also in somewhat advanced to considerably advanced dementia. No adverse event was noted.

TABLE 1

Alzheimer-type dementia

| No. | Gender | Age | Diagnosis | Chief complaint, etc. | Dementia history (year) | Dose of EPA-E mg/day | Dose of T4 μg/day | Hasegawa Dementia Scale At the start | After 2 months | After 6 months | Side effects | Concomitant drug | Change in symptom |
|---|---|---|---|---|---|---|---|---|---|---|---|---|---|
| 1 | Female | 60' | Dementia | Forgetfulness | 5 | 300 | 100 | 8 | 9 | 18 | 0 | None | |
| 2 | Female | 50' | Diabetes mellitus, dementia | Forgetfulness | 1 | 600 | 100 | 14 | 14 | 18 | 0 | Insulin | Willingness |
| 3 | Male | 70' | Dementia | Forgetfulness | 5 | 600 | 50 | 4 | 7 | 14 | 0 | None | |
| 4 | Female | 60' | Dementia | Anorexia | 3 | 300 | 100 | 13 | 14 | 16 | 0 | None | |
| 5 | Female | 60' | Dementia | Anorexia | 6 | 600 | 100 | 6 | 8 | 15 | 0 | None | Willingness |
| 6 | Female | 70' | Diabetes mellitus, dementia | Headache | 2 | 600 | 100 | 8 | 11 | 18 | 0 | SU drug | |
| 7 | Female | 60' | Diabetes mellitus, dementia | Diabetes treatment | 4 | 600 | 100 | 8 | 11 | 17 | 0 | Insulin | Refection |
| 8 | Male | 60' | Dementia, adrenal insufficiency | Dystropy | 1 | 300 | 100 | 12 | 12 | 14 | 0 | Glucocorticoid | |
| 9 | Male | 70' | Dementia | Forgetfulness | 7 | 600 | 50 | 16 | 17 | 22 | 0 | None | Refection |
| 10 | Male | 60' | Diabetes mellitus, dementia | Diabetes treatment | 15 | 300 | 100 | 9 | 11 | 14 | 0 | SU drug | |

TABLE 1-continued

Alzheimer-type dementia

| No. | Gender | Age | Diagnosis | Chief complaint, etc. | Dementia history (year) | Dose of EPA-E mg/day | Dose of T4 μg/day | Hasegawa Dementia Scale At the start | After 2 months | After 6 months | Side effects | Concomitant drug | Change in symptom |
|---|---|---|---|---|---|---|---|---|---|---|---|---|---|
| 11 | Female | 70' | Dementia | Forgetfulness | 5 | 600 | 50 | 10 | 13 | 20 | 0 | None | Increase in the habitat |
| 12 | Male | 80' | Dementia | Forgetfulness | 5 | 300 | 50 | 11 | 10 | 16 | 0 | None | |
| 13 | Female | 70' | Hypertension, dementia | Hypertension treatment | 6 | 600 | 100 | 14 | 15 | 20 | 0 | Ca antagonist | Lucidity |
| 14 | Male | 60' | Diabetes mellitus, dementia | Diabetes treatment | 2 | 300 | 100 | 7 | 7 | 13 | 0 | Insulin | Refection |

Reference Example

Subject and Method 10 patients (6 males and 4 females in their fifties to eighties) diagnosed with cerebrovascular dementia but having the history of cerebral infarction were administered with ethyl icosapentate (trade name Epadel; manufactured by Mochida Pharmaceutical Co., Ltd.; abbreviated as "EPA-E" in the Table) at a daily dose of 300 to 600 mg for 2 months, and then, also with levothyroxine sodium (trade name thyradin S; manufactured by ASKA Pharmaceutical Co., Ltd.; abbreviated as "T4" in the Table) at a daily dose of 50 to 100 μg for 4 months in addition to the ethyl icosapentate. Each patient was evaluated for the improvement of the dementia by Hasegawa Dementia Scale at the start of the test, 2 months after the start of the test (2 months from the start of administering ethyl icosapentate), and 6 months after the start of the test (4 months after the start of the combined administration of the ethyl icosapentate and the levothyroxine sodium).

Results

The results for each case are shown in Table 2. The average score of the Hasegawa Dementia Scale is shown in Table 3 together with the average score of Examples. As shown in Table 2, average score of the Hasegawa Dementia Scale was in slightly improving trend in substantially all cases after 6 months although the improvement was not significant. In the observation of the symptom, refection was noted in one case (10%). The case that showed such improvement of the symptom was the case in which highest score of Hasegawa Dementia Scale had been observed at the start of the test. No adverse event was noted.

TABLE 2

Cerebrovascular dementia

| No. | Gender | Age | Diagnosis | Chief complaint, etc. | Dementia history (year) | Dose of EPA-E mg/day | Dose of T4 μg/day | Hasegawa Dementia Scale At the start | After 2 months | After 6 months | Side effects | Concomitant drug | Change in symptom |
|---|---|---|---|---|---|---|---|---|---|---|---|---|---|
| 1 | Male | 60' | Cerebral infarction, diabetes mellitus, dementia | Disorientation | 2 | 600 | 100 | 8 | 9 | 11 | 0 | Insulin | |
| 2 | Female | 60' | Cerebral infarction, dementia | Paralysis | 2 | 300 | 100 | 12 | 13 | 14 | 0 | None | |
| 3 | Male | 50' | Cerebral infarction, dementia | Slump | 1 | 600 | 100 | 14 | 15 | 18 | 0 | None | Refection |
| 4 | Male | 60' | Cerebral infarction, dementia | Forgetfulness | 4 | 600 | 100 | 10 | 11 | 12 | 0 | None | |
| 5 | Female | 70' | Cerebral infarction, dementia | Disorientation | 9 | 600 | 50 | 10 | 12 | 14 | 0 | None | |
| 6 | Male | 60' | Cerebral infarction, diabetes mellitus, dementia | Weight loss | 6 | 300 | 100 | 10 | 10 | 11 | 0 | Insulin | |
| 7 | Female | 70' | Cerebral infarction, dementia | Weight loss | 1.5 | 300 | 50 | 11 | 12 | 13 | 0 | None | |
| 8 | Female | 80' | Cerebral infarction, dementia | Disorientation | 10 | 300 | 50 | 9 | 10 | 11 | 0 | None | |

TABLE 2-continued

Cerebrovascular dementia

| | | | | Chief complaint, etc. | Dementia history (year) | Dose of EPA-E mg/day | Dose of T4 μg/day | Hasegawa Dementia Scale | | | Side effects | Concomitant drug | Change in symptom |
|---|---|---|---|---|---|---|---|---|---|---|---|---|---|
| No. | Gender | Age | Diagnosis | | | | | At the start | After 2 months | After 6 months | | | |
| 9 | Male | 70' | Cerebral infarction, dementia | Paralysis | 5 | 600 | 50 | 9 | 9 | 13 | 0 | None | |
| 10 | Male | 60' | Cerebral infarction, diabetes mellitus, dementia | Insomnia | 3 | 600 | 100 | 11 | 11 | 14 | 0 | SU drug | |

TABLE 3

Score of the Hasegawa Dementia Scale
(average ± standard deviation, range)

| | At the start of the test | 2 months after the start of the test | 6 months after the start of the test |
|---|---|---|---|
| Examples (Alzheimer-type dementia) | 10.0 ± 3.5 (6-16) | 11.4 ± 3.0 (7-17) | 16.8 ± 2.7 (13-22) |
| Referential Examples (Cerebrovascular dementia) | 10.4 ± 1.7 (9-14) | 11.2 ± 1.9 (9-15) | 13.1 ± 2.1 (11-18) |

As demonstrated by the results of Table 3, while sole administration of ethyl icosapentate at a dose of 300 to 600 mg/day for 2 months resulted in no substantial change in the scores of the Hasegawa Dementia Scale of the patients suffering from Alzheimer-type dementia, simultaneous administration of levothyroxine sodium for the subsequent 4 months at a dose of 50 to 100 μg/day with the ethyl icosapentate resulted in the significant improvement in the scores of the Hasegawa Dementia Scale of the patients suffering from Alzheimer-type dementia. On the other hand, as demonstrated by the results of the Referential Example in Table 3, only slight improvement in the score of Hasegawa Dementia Scale was realized in test of the simultaneous administration of the ethyl icosapentate at 300 to 600 mg/day and the levothyroxine sodium at 50 to 100 μg/day for the patients of cerebrovascular dementia.

As demonstrated above, the combination of an ω-3 polyunsaturated fatty acid and a thyroid hormone, and in particular, the combination of the EPA-E and the levothyroxine sodium has a significant therapeutic effects for Alzheimer-type dementia with no adverse event, and such combination would constitute a highly effective and safe preventive or therapeutic drug for Alzheimer-type dementia. In the meanwhile, since the daily dose of the EPA-E for present indication, namely, hyperlipidemia or arteriosclerosis obliterans (ASO) is 1800 to 2700 mg, the results confirmed that EPA-E exhibits its effect at a dose lower than the usual dose when combined with the levothyroxine sodium. In addition, since usual dose (maintenance dose) of the levothyroxine sodium for present indication is 100 to 400 μg/day, the levothyroxine sodium exhibits was also confirmed to exhibit its effect at the lower limit of the usual dose or at an even lower dose.

The invention claimed is:

1. A therapeutic method for treating Alzheimer-type dementia comprising:
   administering an ethyl ester of an ω-3 polyunsaturated fatty acid and a salt of a thyroid hormone, wherein the ethyl ester is ethyl icosapentate and the salt of a thyroid hormone is levothyroxine sodium, and wherein the dose of ethyl icosapentate is 300 to 600 mg/day and the dose of levothyroxine sodium is 25 to 100 μg/day.

2. A therapeutic method for treating Alzheimer-type dementia comprising:
   administering an ethyl ester of an ω-3 polyunsaturated fatty acid and a salt of a thyroid hormone, wherein the ethyl ester is ethyl icosapentate and the salt of a thyroid hormone is levothyroxine sodium, and wherein the dose of ethyl icosapentate is 300 to 600 mg/day and/or the dose of levothyroxine sodium is 25 to 200 μg/day.

3. The therapeutic method according to claim 1, wherein 300 to 600 mg of ethyl icosapentate and 50 to 100 μg of levothyroxine sodium are administered daily.

4. The therapeutic method according to claim 1, wherein at least 85% by weight of the fatty acid composition is ethyl icosapentate.

5. The therapeutic method according to claim 1, wherein the ω-3 polyunsaturated fatty acid, the ethyl ester of an ω-3 polyunsaturated fatty acid, or the salt thereof is a component of a first composition and the thyroid hormone or the salt thereof is a component of a second composition, and the first composition and the second composition are administered to the subject separately.

6. The therapeutic method according to claim 1, wherein administering the ethyl icosapentate in combination with the levothyroxine sodium continues for at least 4 months.

* * * * *